United States Patent
Skibin et al.

(10) Patent No.: US 9,494,537 B2
(45) Date of Patent: Nov. 15, 2016

(54) METHOD FOR DETERMINING THE THERMAL CONDUCTIVITY OF AN IMPREGNATED POROUS MEDIUM

(75) Inventors: Alexander Petrovich Skibin, Moscow (RU); Darya Aleksandrovna Mustafina, Perm (RU); Aleksandra Evgenievna Komrakova, Moscow (RU)

(73) Assignee: Schlumberger Technology Corporation, Sugar Land, TX (US)

( * ) Notice: Subject to any disclaimer, the term of this patent is extended or adjusted under 35 U.S.C. 154(b) by 645 days.

(21) Appl. No.: 13/977,636

(22) PCT Filed: Dec. 30, 2010

(86) PCT No.: PCT/RU2010/000804
§ 371 (c)(1),
(2), (4) Date: Nov. 8, 2013

(87) PCT Pub. No.: WO2012/091600
PCT Pub. Date: Jul. 5, 2012

(65) Prior Publication Data
US 2014/0056326 A1    Feb. 27, 2014

(51) Int. Cl.
*G01N 25/18*    (2006.01)
(52) U.S. Cl.
CPC ..................... *G01N 25/18* (2013.01)
(58) Field of Classification Search
USPC .......................................... 374/44, 120, 141
See application file for complete search history.

(56) References Cited

U.S. PATENT DOCUMENTS

| | | | |
|---|---|---|---|
| 2010/0080260 A1* | 4/2010 | Skibin | G01N 25/18 374/44 |
| 2013/0094624 A1* | 4/2013 | Skibin | G01N 23/046 378/4 |
| 2015/0049784 A1* | 2/2015 | Popov | G01N 25/18 374/44 |
| 2015/0055676 A1* | 2/2015 | Popov | G01N 25/18 374/44 |

(Continued)

FOREIGN PATENT DOCUMENTS

| | | |
|---|---|---|
| DE | 3204028 A1 | 8/1983 |
| RU | 2190209 C1 | 9/2002 |
| RU | 2277235 C1 | 5/2006 |

OTHER PUBLICATIONS

Clauser, et al., "Thermal Conductivity of Rocks and Minerals", American Geophysical Union, 1995, pp. 105-126.

(Continued)

*Primary Examiner* — Mirellys Jagan

(57) ABSTRACT

This invention relates to methods for determination of thermophysical properties of porous media filled with fluid, gas, or other mineral medium, and can be used, in particular, in the oil and gas industry. When implementing the method, it is necessary to initially determine a composition of a saturated porous medium and thermal conductivity coefficients of its components. A three-dimensional image of a sample of the porous medium is obtained by X-ray scanning. A thermal conductivity coefficient of the medium is determined by solving thermal conductivity problems, based on decomposition of a computational domain followed by composition.

2 Claims, 3 Drawing Sheets

(56) References Cited

U.S. PATENT DOCUMENTS

2015/0168323 A1* 6/2015 Popov .................. G01N 25/18
374/44

OTHER PUBLICATIONS

Lee, et al., "Modelling of effective thermal conductivity for a nonhomogeneous anisotropic porous medium", International Journal of Heat and Mass Transfer, vol. 41 (6-7), 1998, pp. 931-937.
Sasov, A. Yu., "Microtomography: I. Methods and equipment", Journal of Microscopy, vol. 147 (2), 1987, pp. 169-178.
Sasov, A. Yu., "Microtomography: II. Examples of applications", Journal of Microscopy, vol. 147 (2), 1987, pp. 179-192.
Zhang, et al., "Effective thermal conductivity of two-scale porous media", Applied Physics Letters, vol. 89, 2006, 3 pages.

* cited by examiner

METHOD FOR DETERMINING THE THERMAL CONDUCTIVITY OF AN IMPREGNATED POROUS MEDIUM

CROSS-REFERENCE TO RELATED APPLICATION

This application is a United States National Stage Application under 35 U.S.C. §371 and claims priority to Patent Cooperation Treaty Application Number PCT/RU2010/000804 filed Dec. 30, 2010, which is incorporated herein by reference in its entirety.

FIELD OF THE DISCLOSURE

This invention relates to methods for determination of thermophysical properties of porous media filled with fluid, gas, or other mineral medium. The invention can be used for such porous media as composite materials, geological formations, bone tissues.

The materials are considered to be "porous" if a medium (skeleton) they are composed of, is porous (has pores or discontinuities). These pores can be void, but most often they are filled with some fluids, such as water, oil, gas, etc.

The areas which can be filled with fluid include, in particular, pores, layer fractures, cavities, etc. Water, oil and other liquids can serve as the fluid here. Natural gas, air, or any other gaseous substance can be regarded as the gas. Any solid formation in fixed or bulk condition, having a mineralogical composition, can serve as the mineral medium.

The method can be used in oil and gas industry, in particular, for determination of thermal conductivity of an oil-saturated porous geological medium, in the development of oil and gas fields (injection wells, production wells).

BACKGROUND OF THE DISCLOSURE

Thermal methods for enhanced oil recovery provide for a preliminary modeling of the heat-and-mass exchange processes in a reservoir (an oil reservoir) and in wells, as well as determination of thermal conditions for downhole equipment. So information on thermophysical properties of rock (such as the thermal conductivity, heat capacity and thermal diffusivity) is of primary importance.

There are known methods for determination of the thermal conductivity of porous rock, such as described in S. L. Lee, J. H. Yang, Modeling of effective thermal conductivity for a non-homogeneous anisotropic porous medium, Int. J. Heat Mass Transfer, Vol. 41, Issue 6-7, pp. 931-937, 1998, or described in H. Ye, Effective thermal conductivity of two-scale porous media, APPLIED PHYSICS LETTERS 89, 081908 (2006).

However, the above-mentioned methods allow for determining thermal conductivity of only small-sized samples and are characterized by increased labor requirements and increased time consumption.

SUMMARY OF THE DISCLOSURE

The claimed method for determination of thermal conductivity of a saturated porous medium allows for improving the accuracy of determination of thermal conductivity as compared to known methods, and consists in determining a microstructure of a sample of a porous medium and in solving a thermal conductivity problem, based on decomposition of a computational domain with following composition.

The claimed method comprises the following steps:
determining a composition of a saturated porous medium and thermal conductivity coefficients of determined components,
performing an X-ray scanning of a sample of the saturated porous medium and obtaining a three-dimensional image of the sample which is a first single computational domain and consists of N voxels, with $N=N_x \cdot N_y \cdot N_z$, where $N_x$, $N_y$, $N_z$ are numbers of voxels along x, y, z axes, respectively,
combining the N voxels into n coarse cells, with $n=n_x \cdot n_y \cdot n_z$, where $n_x$, $n_y$, $n_z$ are numbers of coarse cells along the x, y, z axes, respectively, with $2<n_x<N_x$, $2<n_y<N_y$, $2<n_z<N_z$,
solving a first thermal conductivity problem for each of the coarse cells in each of the x, y, z directions, and determining an effective thermal conductivity coefficient in each direction,
combining the coarse cells into a second single computational domain,
solving a second thermal conductivity problem for the second single computational domain which is composed of the coarse cells, and determining an effective thermal conductivity coefficient for the whole computational domain in three directions,
determining a thermal conductivity coefficient of the saturated porous medium as an average of the determined thermal conductivity coefficients along the axes.

DETAILED DESCRIPTION

At first it is necessary to determine a composition of a porous medium and, consequently, thermal conductivity coefficients of determined components of the porous medium. The components can be determined by known methods, such as methods described in the paper by V. N. Shvanov, Petrography of Sandy Rock (Composition, Systematics, and Description of Mineral Species)—Leningrad: Nedra Publishing House, 1987, p. 269. The thermal conductivity coefficients of the determined components are determined from reference literature, e.g., from Clauser, C and E. Huenges, 1995, Thermal Conductivity of Rocks and Minerals, Rock Physics and Phase Relations.

Then, it is necessary to obtain information on microstructure of the porous medium. A rectangular-parallelepiped-shaped sample of the saturated porous medium is taken for tests. Results of this test are usually represented as data on filling of each unit of a computational domain (the sample of the medium represents the computational domain) with one or another material. The unit of the computational domain is selected depending on the test type.

A microstructure of the sample is determined by X-ray scanning of the sample. The X-ray computer tomographs which are used for obtaining the data on the microstructure are described, for example, in http://www.ngi.no/no/Innholdsbokser/Referansjeprosjekter-LISTER-/Referanser/Rock-structure-visualisation-with-CT/A or in the paper by Sasov, Microtomography, Journal of Microscopy, Vol. 147 (2): 169-192, 1987.

Figure 1:
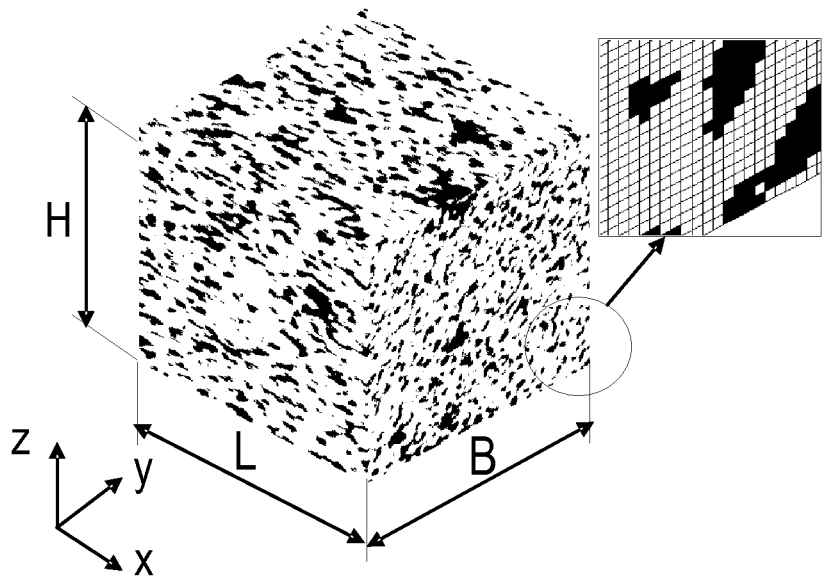
FIG. 1 shows a microstructure of a parallelepiped-shaped sample.

The scanning gives data on the microstructure of the sample having a height H, a length L and a width B in the form of a first three-dimensional computational domain consisting of $N_x \cdot N_y \cdot N_z$ three-dimensional cells (voxels), where $N_x$, $N_y$, $N_z$ are numbers of voxels along x, y, z axes, respectively, with each of these voxels having an edge length equal to a scanning resolution value (FIG. 1). In the microstructure determination, each of these voxels is considered to be filled; that is to say, it is considered to correspond to a certain material from the two-component or multi-component medium being studied, e.g., to a skeleton or a fluid. For example, white color in FIG. 1 corresponds to the skeleton of the porous medium, while black color corresponds to the fluid in pores. Consequently, the thermal conductivity coefficients of each of the voxels are considered to be known.

Figure 2:
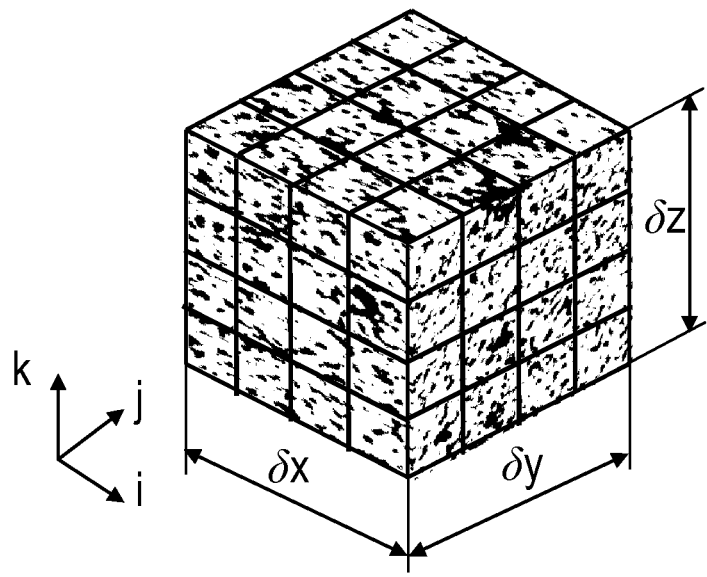
FIG. 2 shows decomposition of a computational domain.

FIG. 2 shows decomposition of the first computational domain having a length δx, a width δy and a height δz, in the course of which $N_x \cdot N_y \cdot N_z$ voxels of the first computational domain are combined into $n_x \cdot n_y \cdot n_z$ of coarse cells having dimensions of a cell equal to $D_x \cdot D_y \cdot D_z$ in x-, y-, z-axis directions, respectively, so that a number of the coarse cells along a respective axis meets the following inequalities: $2 < n_x < N_x$, $2 < n_y < N_y$, $2 < n_z < N_z$.

Figure 3:
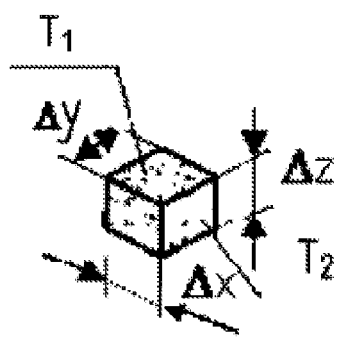
FIG. 3 shows a coarse cell.

For each of these coarse cells (with a number ijk) in each of the x, y, z directions, a first thermal conductivity problem is solved, based on the established assumptions (FIG. 3). A mathematical model of this first thermal conductivity problem consists of a thermal conductivity equation (1) and boundary conditions (2):

$$\text{div}(l^a \text{grad} T) = 0, \tag{1}$$

where $l^a$ is a thermal conductivity coefficient which is defined according to the X-ray scanning results for each voxel; a is a voxel number in a coarse cell (for example, in case of a two-component medium, we assume that a=1 corresponds to a skeleton, while a=0 corresponds to a pore-filling material); T is a temperature; div, grad are mathematical operators.

Figure 4:
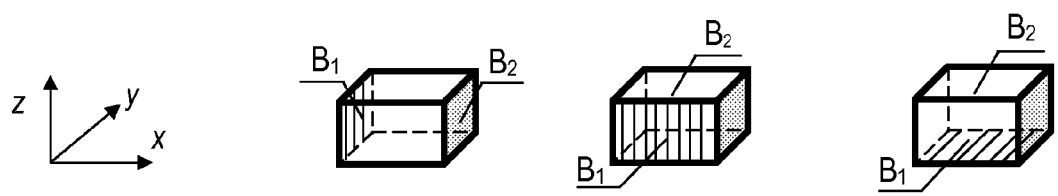
FIG. 4 shows boundaries for x, y, z directions.
Figure 5:
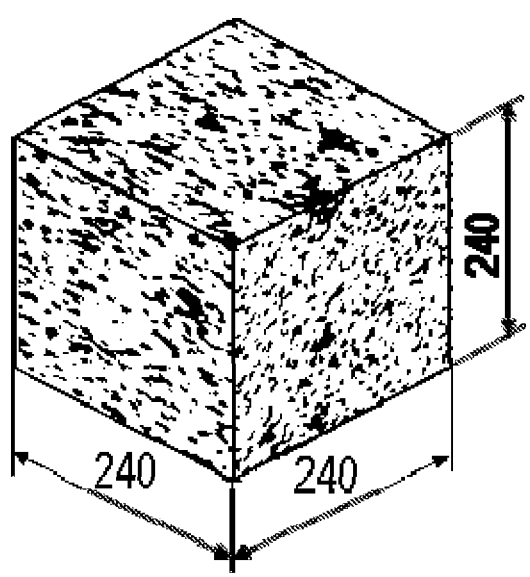
FIG. 5 shows a rock sample 240×240×240 mm in size.

The boundary conditions are established as follows (FIG. 4). In each of the x, y, z directions, a first cell surface perpendicular to an axis under consideration is considered to be $B_1$, and an opposite surface is considered to be $B_2$. Temperatures on the above-mentioned surfaces are taken equal to $T_1$ и $T_2$, respectively. Other surfaces of the coarse cell are considered to be thermally insulated. So, the boundary conditions are expressed as:

On $B_1$ boundary: $T=T_1$,

On $B_2$ boundary: $T=T_2$,

On all other boundaries: $(l^a \text{grad} T, n) = 0$, (2)

where n is a normal to the boundary surface.

It should be noted at the same time that the mathematical model of the first thermal conductivity problem for the first computational domain is built, based on the following important assumptions: a heat flux propagates in a direction under consideration only, i.e., we assume that the heat flux propagates along the coordinate axis (x, y, z) for which the current equation is set up; principal axes of anisotropy coincide with the coordinate axes (i.e. a length of irregularity in properties coincides with the x, y, z coordinate axes).

Temperature fields, from which fields of normal temperature derivatives with respect to the boundary surfaces of a coarse cell are calculated, are the solution to the mathematical model consisting of the thermal conductivity equations (1) and the boundary conditions (2) based on the adopted assumptions.

A heat flux that passes across a boundary of a coarse cell in the x, y, z directions is determined through an area integral of a temperature derivative in the corresponding directions (axes) and is equal to:

$$Q_x^{ijk} = \int_{S_{yz}} l^a \frac{\partial T}{\partial x} dS, \; Q_y^{ijk} = \int_{S_{xz}} l^a \frac{\partial T}{\partial y} dS, \; Q_z^{ijk} = \int_{S_{xy}} l^a \frac{\partial T}{\partial z} dS,$$

where $S_{yz}$ is an area of the sample surface perpendicular to the x axis, $S_{xz}$ is an area of the sample surface perpendicular to the y axis, $S_{xy}$, is an area of the sample surface perpendicular to the z axis.

In case of a macroscopic description of the porous medium, the heat propagation is described by Fourier's law, wherein a thermal conductivity tensor is replaced with an effective thermal conductivity tensor.

For each of the coarse cells, a heat propagation described by Fourier's law is given by:

$$l_{x,\mathfrak{I}\phi}^{ijk} = \frac{Q_x^{ijk} Dx}{(T_2 - T_1) DyDz},$$

$$l_{y,\mathfrak{I}\phi}^{ijk} = \frac{Q_y^{ijk} Dy}{(T_2 - T_1) DxDz},$$

$$l_{z,\mathfrak{I}\phi}^{ijk} = \frac{Q_z^{ijk} Dz}{(T_2 - T_1) DxDy},$$

where $l_{x,\mathfrak{I}\phi}^{ijk}$, $l_{y,\mathfrak{I}\phi}^{ijk}$, $l_{z,\mathfrak{I}\phi}^{ijk}$ are effective thermal conductivity coefficients in the x, y, z directions, respectively.

A next operation of the method is to combine the coarse cells into a second single computational domain, while considering that each of the coarse cells is homogeneous and has the thermal conductivity coefficient equal to the effective thermal conductivity coefficient in each of such cells.

Then, a second thermal conductivity problem is solved for the second combined computational domain which is composed of the coarse cells. A mathematical model of this second thermal conductivity problem consists of a thermal conductivity equation for the second combined computational domain and is given by:

$$\text{div}([l_{\mathfrak{I}\phi}^{ijk}] \text{grad} T) = 0,$$

and of boundary conditions which represent given $T_1$ and $T_2$ temperatures on the first surface perpendicular to the axis under consideration (x, y, z) and on the opposite surface, respectively, while all other surfaces are considered to be thermally insulated.

The assumptions that the heat flux propagates in the direction under consideration only (along the x, y, z axis) and that the main axes of anisotropy match the coordinate axes, remain in force.

A heat flux that passes across the boundaries of the second combined computation domain in the x, y, z directions is equal to:

$$Q_x = \int_{S'_{yz}} l_{x,\mathfrak{I}\phi}^{ijk} \frac{\partial T}{\partial x} dS, \; Q_y = \int_{S'_{xz}} l_{y,\mathfrak{I}\phi}^{ijk} \frac{\partial T}{\partial y} dS, \; Q_z = \int_{S'_{xy}} l_{z,\mathfrak{I}\phi}^{ijk} \frac{\partial T}{\partial z} dS,$$

where $S'_{yz}$ is an area of the sample surface perpendicular to the x axis, $S'_{xz}$ is an area of the sample surface perpendicular to the y axis, $S'_{xy}$ is an area of the sample surface perpendicular to the z axis.

When solving the second thermal conductivity problem in combination with the boundary conditions based on the above-mentioned assumptions, we determine effective thermal conductivity coefficients for the whole computational domain in three (x, y, z) directions:

$$l_{x \ni \phi} = \frac{Q_x dx}{(T_2 - T_1) dy dz},$$

$$l_{y \ni \phi} = \frac{Q_y dy}{(T_2 - T_1) dx dz},$$

$$l_{z \ni \phi} = \frac{Q_z dz}{(T_2 - T_1) dx dy},$$

where δx, δy, δz are sample dimensions.

A thermal conductivity coefficient of the medium is equal to the average of the thermal conductivity coefficients determined along each of the coordinate axes, namely:

$$l = \frac{1}{3} * (l_x^{ijk}{}_{\ni \phi} + l_y^{ijk}{}_{\ni \phi} + l_z^{ijk}{}_{\ni \phi}).$$

The suggested method was tested on samples 240×240×240 mm in size and was applied to samples 1,800×1,800×1,800 mm in size.

For example, a thermal conductivity coefficient was determined by the suggested method for a sample 240×240×240 mm in size.

The number of coarse cells was equal to n=4 along each of coordinate axes, and a total number of coarse cells was equal to 4×4×4=64.

Effective thermal conductivity coefficients were determined for each of the coarse cells in x, y, z directions. The coarse cells were then combined into a single computational domain where each of the coarse cells was represented as a homogeneous material having the thermal conductivity coefficients determined in the previous step. Then, an effective thermal conductivity coefficient of the whole sample was determined in the x, y, z directions. Table 1 shows the values obtained for different filling fluids.

Comparison of the thermal conductivity coefficient determination results with the exact solution shows that the error of determination in the x, y, z directions does not exceed 0.56% for the sample under consideration (Table 1).

Table 2 shows the results of the thermal conductivity coefficient determination for a sample 1,800×1,800×1,800 mm in size, by the suggested method.

TABLE 2

| | Ratio of the thermal conductivity of the saturating fluid to the thermal conductivity of rock, $\lambda_f/\lambda_s$ | |
|---|---|---|
| | 0.01 | 0.247 |
| | $\lambda_{eff}$, (W/m · K) | |
| X direction | 0.562 | 0.750 |
| Y direction | 0.548 | 0.747 |
| Z direction | 0.601 | 0.764 |

The invention claimed is:

1. A method for determination of thermal conductivity of a saturated porous medium, comprising the following steps:
    determining components forming a composition of the saturated porous medium and thermal conductivity coefficients of the determined components;
    performing an X-ray scan of a sample of the saturated porous medium and obtaining a three-dimensional image of the sample which is a first single computational domain and consists of N voxels, with $N=N_x \cdot N_y \cdot N_z$, $N_z$, where $N_x$, $N_y$, $N_z$ are numbers of voxels along x, y, z axes, respectively;
    combining the N voxels into n coarse cells, with $n=n_x \cdot n_y \cdot n_z$, $n_z$, $n_x$, $n_y$, $n_z$, are numbers of coarse cells along the x, y, z axes, respectively, with $2<n_x<N_x$, $2<n_y<N_y$, $2<n_z<N_z$;
    solving a first thermal conductivity problem for each of the coarse cells in each of the x, y, z directions and determining effective thermal conductivity coefficients in each direction;
    combining the coarse cells into a second single computational domain;
    solving a second thermal conductivity problem for the second single computational domain which is composed of the coarse cells and determining effective

TABLE 1

| X direction | | | | | | | |
|---|---|---|---|---|---|---|---|
| Ratio of the thermal conductivity of the saturating fluid to the thermal conductivity of rock, $\lambda_f/\lambda_s$ | 0.01 | 0.1 | 0.247 | 0.5 | 0.75 | 0.99 | 1 |
| Suggested method, $\lambda_{x\ eff}/\lambda_s$ | 0.555 | 0.650 | 0.747 | 0.856 | 0.936 | 0.998 | 1 |
| Exact solution, $\lambda_{x\ eff}/\lambda_s$ | 0.556 | 0.649 | 0.747 | 0.857 | 0.936 | 0.998 | 1 |
| Error, % | 0.135 | 0.081 | 0.043 | 0.006 | 0.001 | 0.008 | 0 |
| Y direction | | | | | | | |
| Ratio of the thermal conductivity of the saturating fluid to the thermal conductivity of rock, $\lambda_f/\lambda_s$ | 0.01 | 0.1 | 0.247 | 0.5 | 0.75 | 0.99 | 1 |
| Suggested method, $\lambda_{y\ eff}/\lambda_s$ | 0.549 | 0.649 | 0.747 | 0.857 | 0.936 | 0.998 | 1 |
| Exact solution, $\lambda_{y\ eff}/\lambda_s$ | 0.553 | 0.649 | 0.747 | 0.857 | 0.936 | 0.998 | 1 |
| Error, % | 0.559 | 0.094 | 0.018 | 0.008 | 0.004 | 0.008 | 0 |
| Z direction | | | | | | | |
| Ratio of the thermal conductivity of the saturating fluid to the thermal conductivity of rock, $\lambda_f/\lambda_s$ | 0.01 | 0.1 | 0.247 | 0.5 | 0.75 | 0.99 | 1 |
| Suggested method, $\lambda_{z\ eff}/\lambda_s$ | 0.607 | 0.684 | 0.765 | 0.863 | 0.937 | 0.998 | 1 |
| Exact solution, $\lambda_{z\ eff}/\lambda_s$ | 0.608 | 0.684 | 0.766 | 0.863 | 0.937 | 0.998 | 1 |
| Error, % | 0.171 | 0.074 | 0.052 | 0.023 | 0.007 | 0.009 | 0 | thermal conductivity coefficients for the whole computational domain in three directions; and determining a thermal conductivity coefficient of the saturated porous medium as the average of the determined thermal conductivity coefficients along the coordinate axes.

2. The method of claim 1, wherein the saturated porous medium is a rock.

* * * * *